United States Patent [19]

Lane

[11] 4,226,983
[45] Oct. 7, 1980

[54] PREPARATION OF METAL COMPLEXES
[75] Inventor: Edward S. Lane, Didcot, England
[73] Assignee: United Kingdom Atomic Energy Authority, London, England
[21] Appl. No.: 945,841
[22] Filed: Sep. 26, 1978
[30] Foreign Application Priority Data

Sep. 29, 1977 [GB] United Kingdom ............... 40587/77

[51] Int. Cl.³ .................................................. C08B 37/02
[52] U.S. Cl. .............................. 536/113; 260/439 R; 424/180; 536/102; 536/103; 536/112
[58] Field of Search ............... 536/112, 113, 102, 103; 424/180; 260/439 R

[56] References Cited

U.S. PATENT DOCUMENTS

| | | | |
|---|---|---|---|
| 2,885,393 | 5/1959 | Herb | 536/113 |
| 3,536,696 | 10/1970 | Alsop et al. | 536/112 |
| 3,549,614 | 12/1970 | Mioduszewski et al. | 536/113 |
| 3,697,502 | 10/1972 | Christensen | 536/113 |
| 3,928,581 | 12/1975 | Dahlberg et al. | 536/112 |
| 4,094,832 | 6/1978 | Soderberg | 536/112 |

FOREIGN PATENT DOCUMENTS 573374  3/1959  Canada ................................ 536/112

*Primary Examiner*—Johnnie R. Brown
*Attorney, Agent, or Firm*—Larson, Taylor and Hinds

[57] ABSTRACT

A process is disclosed for the preparation of a complex of an element in solution, said complex including the element and an organic complexing agent, which process comprises treating a gel precipitate containing the element and an organic complexing agent to redisperse the gel precipitate into solution.

10 Claims, No Drawings

PREPARATION OF METAL COMPLEXES

The present invention relates to compounds and their preparation and in particular to compounds which are complexes and their preparation.

According to one aspect of the present invention a process for the preparation of a complex of an element in solution, said complex including the element and an organic complexing agent, comprises treating a gel precipitate containing the element and an organic complexing agent to redisperse the gel precipitate into solution.

According to another aspect of the present invention a process for the preparation of a complex of an element in solution, said complex including the element and an organic complexing agent comprises forming a gel precipitate containing the element and an organic complexing agent and treating the gel precipitate to redisperse it into solution.

The organic complexing agent may be, for example polymeric or non-polymeric. When the organic complexing agent is a polymeric organic complexing agent the invention provides a process for the preparation of a complex of an element in solution, said complex including the element and a polymeric organic complexing agent, which process comprises treating a gel precipitate containing the element and a polymeric organic complexing agent to redisperse the gel precipitate into solution.

It will be appreciated that in the gel precipitate the element and organic complexing agent, or polymeric organic complexing agent, as the case may be, will be in the intimate association characteristic of gel precipitates and will have undergone complex formation.

In gel precipitation processes the element in the gel precipitate will generally not be present as the element as such in intimate association with the organic complexing agent, but will be present rather as a compound (e.g. an oxide, hydrous oxide or hydroxide) which is in intimate association with the organic complexing agent.

Thus, in the Specification the phrase "a gel precipitate containing the element and an organic complexing agent" embraces where the gel precipitate contains an element as such and an organic complexing agent, and/or where the gel precipitate contains a compound of an element and an organic complexing agent.

Similarly, while the complex in solution formed by redispersing a gel precipitate in accordance with the present invention may be, under some circumstances, a complex of an element as such and an organic complexing agent, in general the complex in solution will be a complex of a compound of an element and an organic complexing agent.

Thus, for example, in one embodiment a gel precipitate containing an iron compound and an organic complexing agent may be redispersed to give a solution containing a complex of an iron compound (e.g. in the form of a hydrous iron oxide) and an organic complexing agent.

It is preferred, in accordance with the present invention, that the chosen element is such that it is capable of forming a strong complex with a chosen organic complexing agent, or can form a compound capable of forming a strong complex with a chosen organic complexing agent.

By strong complexes we mean complexes such as those which show stability with regard to hydrolysis and are stable to storage (i.e. do not readily separate into distinct components over relatively long periods of time (e.g. may weeks)). An example of such an element is iron.

Strong complexes generally have physical and chemical properties which are significantly different from the physical and chemical properties of the element or compound of the element used to form the complex. It will be appreciated that in forming such complexes the physical and chemical properties of the element or compound of the element used may be significantly altered by the organic complexing agent.

"Solution" as used in this Specification embraces colloidal solutions (sols) and anion deficient solutions as well as "true" solutions.

A gel precipitate may be formed in a number of ways and for details of processes for producing gel precipitates reference may be made to our following British Patent Specifications Nos. 1,175,834, 1,231,385, 1,253,807, 1,313,750, 1,363,532, 1,277,420, and 1,350,389.

Briefly, in the production of a gel precipitate by one form of gel precipitation process (sometimes called "forward" gel precipitation) a feed solution containing an element or a compound of an element (the element typically being a metal) in the form of either a salt solution or a sol, and an organic gelling agent (gelating agent), or agents, is introduced into a precipitating agent to give a gel precipitate containing the element and the gelling agent in intimate association.

The organic gelling agent enables the feed solution to gel in a coherent manner in the presence of a precipitating agent. Such gelling agents are usually water soluble high molecular weight polymeric organic compounds as disclosed in our British Patent Specifications hereinbefore mentioned (e.g. dextran, polyvinyl alcohol, dextrin and starch). Other gelling agents which are not polymeric may be used (e.g. dextrose and sorbitol).

It will be appreciated from the foregoing statements that the organic gelling agent is preferably the organic complexing agent. Thus, examples of polymeric organic complexing agents for use in accordance with the present invention are dextran, polyvinyl alcohol, dextrin and starch, and examples of non-polymeric organic complexing agents are dextrose and sorbitol.

In one embodiment the element may be a metal (e.g. iron).

The gel precipitate may be redispersed into solution, for example, by treatment with an acid or an alkali. The redispersion may be in some cases regarded as peptisation.

According to a preferred embodiment of the present invention there is provided a process for the production of iron dextran solution comprising treating a gel precipitate containing iron and dextran with an acid to redisperse the gel precipitate into solution.

The acid may be for example citric acid, ascorbic acid, tartaric acid, lactic acid or gluconic acid.

It will be appreciated that where the redispersion involves the use of a reagent which is itself a complexing agent (e.g. citrate) the resulting complex in solution may include a complex of the element and the reagent.

It will be appreciated that in accordance with the foregoing embodiment soluble iron dextran is produced by redispersion of the insoluble gel precipitate containing iron dextran.

The gel precipitate containing the iron and dextran may be prepared for example by contacting a feed solution containing a ferric salt and dextran with a precipitating agent such as ammonia.

Known methods for the production of iron dextran in solution, primarily for ingestion, include:
(i) Precipitation of ferric hyroxide by reacting a solution containing ferric ions with an hydroxide (e.g. ammonium hydroxide) and subsequently stirring and heating the precipitate with dextran to peptise the precipitate to give a so-called "ferric dextran" solution.
(ii) Making a mixture of ferric ions, hydroxide ions and dextran (without causing precipitation and dialysing the mixture to remove anions and cause concentration to give a so-called "ferric dextran" solution.

Iron dextrose may be prepared in accordance with the present invention by a process comprising treating a gel precipitate containing iron and dextose with an acid to redisperse the gel precipitate into solution.

It is believed that the process of the present invention, in accordance with one preferred embodiment hereinbefore disclosed, provides a route for the preparation of iron dextran in solution, for ingestion, which is simpler than (i) and less expensive than (ii).

A solution of a complex of an element prepared in accordance with the present invention may be dried to give a solid product. The solid product may be redispersed (e.g. in water) to give a solution of the complex of the element.

Thus, according to yet a further aspect of the present invention there is provided a process for the production of a solid product comprising a complex including an element and an organic complexing agent which includes drying a solution prepared by redispersing into solution a gel precipitate containing the element and an organic complexing agent.

According to yet a further aspect the invention provides a complex of an element in solution, or a solid product derived therefrom, whenever prepared by a process in accordance with the present invention.

It will be appreciated that more than one organic complexing agent may be used in accordance with the present invention. Thus a mixture of complexes of the element can be prepared comprising a mixture of complexes including the element and an organic complexing agents. For example, a mixture of iron dextrose and iron dextran may be prepared by use of a mixture of dextrose and dextran.

It is believed that a dextran "fermentation mixture" (derived by fermenting sucrose (with added ammonium salts) with a micro-organism to give, inter alia, dextran) can be used in accordance with the present invention to form a mixture of iron complexes (including iron dextran) without the separation of dextran from the "fermentation mixture". Such a "fermentation mixture" would contain, inter alia, sucrose, dextran and dextrose.

The invention will now be further described, by way of example only, as follows:

EXAMPLE

A mixture was formed by dissolving 10 g or food quality dextran and 250 g of iron (III) sulphate in water and making up to 2 liters in volume with water. 250 mls of 0.880 S.G. ammonia were diluted to 2 liters with water and added with stirring to the stirred aqueous mixture of ferric sulphate and dextran. A dark brown precipitate formed which filtered easily through filter paper (Whatman 541) and this precipitate was washed with a total of 5 liters of water. The resulting cake of precipitate was transferred to a flask with 600 mls of water and 50 mls concentrated hydrochloric acid, and the contents of the flask stirred at 60° C. After three hours a clear viscous dark red-brown liquid was obtained in the flask. When air-dried at room temperature the contents of the flask gave a trasparent glassy solid which could be redispersed in water.

I claim:
1. A process for the preparation of a solution of a complex of iron, said complex including the iron and an organic complexing agent, comprising treating with an acid or alkali a water-insoluble, gel precipitate containing the iron and an organic complexing agent selected from the group consisting of dextran, polyvinyl alcohol, dextrin, starch, dextrose and sorbitol to redisperse the gel precipitate and form said solution.
2. A process for the preparation of a complex of an element in solution as claimed in claim 1 including the additional step of forming the gel precipitate for treatment.
3. A process as claimed in claim 1 wherein the gel precipitate is dispersed into solution by treatment with an acid or an alkali.
4. A process in accordance with claim 1 for the production of iron dextran solution comprising treating a water-insoluble gel precipitate containing iron and dextran with an acid to redisperse the gel precipitate into solution.
5. A process as claimed in claim 3 wherein the acid is seected from the group consisting of citric acid, ascorbic acid, tartaric acid, lactic acid and gluconic acid.
6. A process as claimed in claim 4 wherein the gel precipitate containing iron and dextran is prepared by contacting a feed solution containing a ferric salt and dextran with a precipitating agent.
7. A process as claimed in claim 6 wherein the precipitating agent is ammonia.
8. A process as claimed in claim 1 wherein more than one organic complexing agent is used.
9. A process in accordance with claim 1 for the production of iron dextrose solution comprising treating a water-insoluble gel precipitate containing iron and dextrose with an acid to redisperse the gel precipitate into solution.
10. A process for the production of a solid product comprising a complex including a metal and an organic complexing agent which comprises drying the solution of claim 1.

* * * * *